United States Patent [19]

Bernstein

[11] Patent Number: 4,770,853
[45] Date of Patent: Sep. 13, 1988

[54] DEVICE FOR SELF CONTAINED SOLID PHASE IMMUNODIFFUSION ASSAY

[75] Inventor: David Bernstein, Sykesville, Md.

[73] Assignee: New Horizons Diagnostics Corporation, Columbia, Md.

[21] Appl. No.: 938,003

[22] Filed: Dec. 3, 1986

[51] Int. Cl.$^4$ .............................................. G01N 21/01
[52] U.S. Cl. ...................................... 422/58; 422/61; 422/102; 435/295
[58] Field of Search ............................ 422/58, 61, 102; 435/294, 295; 206/209, 210, 15.2, 361, 438

[56] References Cited

U.S. PATENT DOCUMENTS

| | | | |
|---|---|---|---|
| 4,150,950 | 4/1979 | Takeguchi et al. | 422/102 X |
| 4,184,483 | 1/1980 | Greenspan | 435/295 X |
| 4,196,167 | 4/1980 | Olsen | 422/61 |
| 4,223,093 | 9/1980 | Newman et al. | 435/294 X |
| 4,224,304 | 9/1980 | Sawai et al. | 422/58 X |
| 4,313,929 | 2/1982 | Morita et al. | 422/56 X |
| 4,353,868 | 10/1982 | Joslin et al. | 422/102 X |
| 4,355,113 | 10/1982 | Mennen | 435/295 |
| 4,391,904 | 7/1983 | Litman et al. | 422/55 X |
| 4,409,988 | 10/1983 | Greenspan | 435/294 X |

Primary Examiner—Barry S. Richman
Assistant Examiner—Timothy M. McMahon
Attorney, Agent, or Firm—Roylance, Abrams, Berdo & Goodman

[57] ABSTRACT

A device for a self contained solid phase immunodiffusion assay. The device is comprised of a sample collector, a tube with compartmentalized reagents and a ligand receptor capture membrane filter area. The seals can be broken through pressure on the sample collector. The sample collector is pushed through the seals, mixed with reagent, and then pushed into a ligand receptor reaction area wherein the tip of the sample collector contacts diffusable membranes or filters and transfers the reactants to a capture membrane wherein a ligand receptor reaction can be visualized by the naked eye.

13 Claims, 1 Drawing Sheet

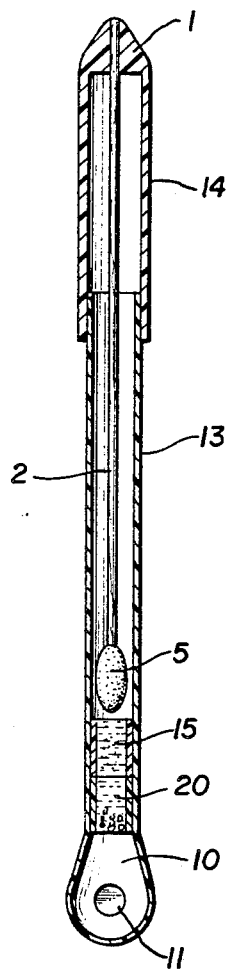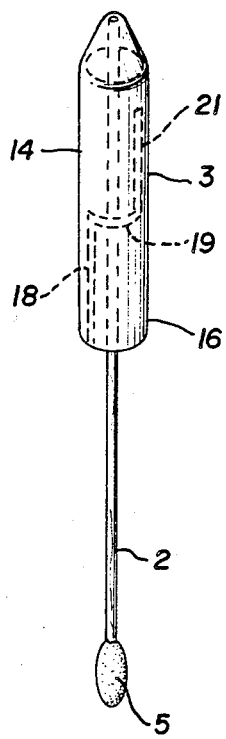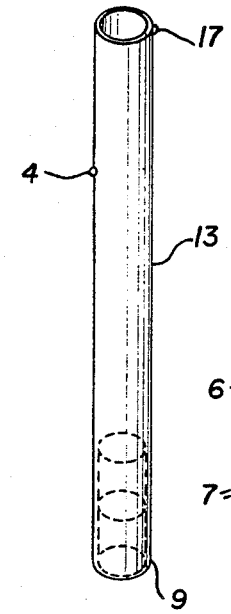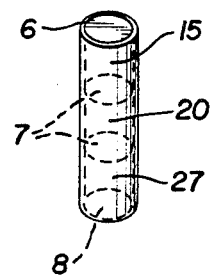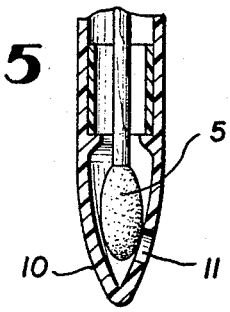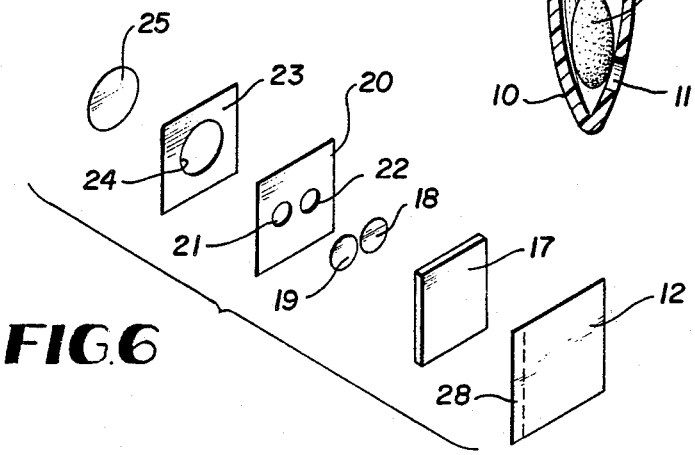

4,770,853

DEVICE FOR SELF CONTAINED SOLID PHASE IMMUNODIFFUSION ASSAY

BACKGROUND OF THE INVENTION

In order to determine the condition of a patient, and to minimize the diseased state, the need for a rapid diagnosis and appropriate treatment by health care professionals is apparent. Diagnosis of many conditions can be facilitated through the determination or quantitation of antibodies, antigens, nucleotide fragments, and analytes from a biological specimen, which are indicative of a particular disease state or condition. A rapid, sensitive, specific, and simplistic assay is extremely useful for emergency situations, field testing, physicians offices and in home diagnostics. As diagnostic tests become more simple and easier to perform, they are being performed away from the professional clinical laboratory setting to physicians offices and even to the home, where untrained or poorly trained individuals perform the tests usually following product insert instructions alone. These assays are useful provided they are performed properly and are safe to handle for the user. Assays that require multiple steps, have multiple reagents, and have limited storage conditions are prone to misuse, especially if they are performed by individuals without adequate training or skills.

Many types of ligand receptor assays have been developed and commercialized. These assays are less expensive if capital equipment can be eliminated, such as scintillation counters, fluorometers, and colorimeters in the case of radioimmunoassay, fluorescent immunoassay, and enzyme immunoassay respectively. Non instrumental assays, such as latex agglutination, enzyme immunoassays on strips, tubes, membranes or filters have increased the usefulness and ease of performance of immunodiagnostic testing, but are still cumbersome requiring washing steps, multiple reagent additions and usually refrigerated storage conditions.

In some assays amplification or growth of viruses and bacteria are desirable before testing to increase the sensitivity of detection. In other assays adsorption steps to remove interferring substances or inhibitors of the ligand receptor assay, or long incubation of reagents are necessary to perform an assay. Each step for an assay increases the difficulty of testing for the minimally trained individual and any device that would reduce user error would improve diagnostic testing.

Horrisberger et al (J. Histo Cytochem volume 25: 295-305, 1977) described the use of colloidal gold particles in an immunoassay. Leuvering in U.S. Pat. No. 4,313,734 also describe such an immunoassay. Cerny in U.S. patent application Ser. No. 850,253 describes a solid phase immunodiffusion assay using gold sol particles as an immunolabel which can be visualized by the naked eye on a capture membrane, and requires no washing step. Bernstein et al (86th annual American Society for Microbiology Meeting, 1986) presented and described a rapid immunodiffusion enzyme labeled antibody assay for Group A Streptococci on a membrane in which there is no washing step. Gould and Zuk in U.S. Pat. No. 4,552,839 describe the use of colored or dyed beads in a solid phase immunoassay. Through the introduction of colored immunolabelled binding reagents (i.e. gold sol particles, dyed particles, dye encapsulated liposomes, etc.) and the removal of washing steps it becomes possible to perform receptor ligand assays in a closed system with the sequential additions of all reagents within that system.

A number of antigens of interest in the diagnosis of infectious disease are collected with a sterile swab on a shaft to remove the organisms from the suspected infected area or test site (wounds, lesions, blood, tissues, pus, fluids, etc.). The swab is generally used to transfer organisms to a suitable media for culturing which may take as long as 48 hours for growth of bacteria, and 2 weeks for viruses. If the organisms are viable and do grow, then their identification could be made by biochemical, morphological or immunological methods. This time consuming method is slowly becoming replaced by more rapid immunological testing methods or DNA probe methodologies.

In many immunoassays that utilize a swab for collection of antigens or cells, the swab is placed in a solution to release the antigenic materials or cells after collection. It may be necessary to use enzymes, acids, detergents, etc. to solubilize or breakdown the antigens to expose antigenic determinants. The extracted material can then be used in an immunoassay by removing the fluid from the swab and mixing it with other reagents or adding the other reagents directly to the swab extract. In the case where membranes or filters are used to capture the immunoreactants, it is necessary to bring the fluid containing the immunoreactants in contact with the filter or membrane.

In addition, where extraneous cells or debris may interfere with an assay, it may be necessary to have a prefilter (larger pore size filter or membrane) present between the swab and the capture membrane or capture filter to retain these unwanted components.

In some assays, where antigen expression may be low, amplification can be achieved if the organisms are first cultured and then tested. If the culturing and the testing could be performed in a single device, then testing would be simplified. In some assays where there are inhibitors, cross reactive products, or clotting factors, red blood cells, etc., it may be necessary to add adsorbant materials (i.e. beads, kaolin, antibody coated particles, antigen coated particles, or lectin coated particles), anticoagulants, or buffers etc. before the ligand receptor assay can be performed.

It is therefore an object of the present invention to provide a novel test device that utilizes a swab or swab-like material (a shaft with a porous or fibrous absorbant material at one end) to collect a sample and to be able to react the swab with all the necessary reagents which are included within the device, and then to use the swab to transfer the reactants sequentially to other reactants if necessary, and finally to a reaction zone where the specific labelled reactant can be captured and visualized.

It is a further object of the present invention to provide a test device useful in performing ligand receptor assays to detect antigens, haptens, antibodies, DNA or RNA fragments, wherein the user is not required to dispense any of the reagents.

It is a particular object of the present invention to provide a test device that can be stored at nonrefrigerated temperatures, and can be utilized to perform an assay on a biological specimen or fluid without any additional reagents having to be provided to the test device.

In addition it is a further object of the present invention to provide a test device which can utilize lyophilized reagents that can be reconstituted in situ within the device.

BRIEF DESCRIPTION OF THE INVENTION

The present invention maximizes the safety and ease of performance of ligand receptor assays through the use of an apparatus designed to enable a biological specimen to be obtained by a collection device comprising a shaft and an attached adsorbant or absorbant porous or fibrous material (i.e. rayon, dacron, cotton swab) which is inserted into a cylindrical tube. The cylindrical tube contains a sealed vessel or plurality of sealed vessels in sequential order and which the seal will break away or collapse when pressure of the collection device (swab) is exerted on the seal by physically pushing the collection device into and through each vessel. These sealed vessels may contain media, extraction reagents, diluents, labelled antibodies, labelled antigens, labelled lectins, anticoagulants, adsorbants, inactivators, etc. which mix with the biological specimen collected on the collection device. The reagents in these vessels may be lyophilized, enabling long term storage at non refrigerated temperature. The vessels are fixed in position in the cylindrical tube to enable the seals to be broken when physical pressure is exerted on the shaft of the collection device. The collection device holder has appropriate stop points to allow for the collection device tip to enter the appropriate vessel and mix with its contents. A key feature of the vessels are that the tip and shaft of the collecting device can pass through each of the vessels into a lower portion of the cylindrical tube and an attached lower portion comprising a ligand receptor reaction area. The ligand receptor area is comprised of a capture membrane or a filter that will allow unbound reactants to pass through by diffusion and retain the appropriate labelled members of the binding pair. The capturing membrane or filter may be coated with a member of the binding pair to capture the reactants. If capture particles are used, then the capture filter is utilized to retain the particles and allow unbound free labelled antigen or antibody to diffuse through. A prefilter may be used between the collector tip and the capture or filter to remove any nonspecific binding due to debris. An additional absorbant material can be placed behind the capture membrane to increase the uptake of fluid. In either case a specific volume of reactant can be absorbed by controlling the size of the filters and absorbant materials. The configuration of the lower portion allows the collection device to come into physical contact with the prefilter, capture membrane or capture filter.

DESCRIPTION OF THE DRAWINGS

FIG. 1 is a cross sectional view of the invention showing the collection device holder, the collection device, the tube, the sealed reagent compartments and the lower ligand receptor transfer area.

FIG. 2 is a perspective view of the basic structure of the collection device holder and collection device including the grooves for guiding the movement of the collection device through the apparatus.

FIG. 3 is a perspective view of the basic structure of the tube, its compartmentalized reagents, and the nodule which fits into the groove of the collection device holder.

FIG. 4 is a perspective view of the sealed compartments (i.e. vessels) of the apparatus.

FIG. 5 is a cross sectional side view of the lower portion of the apparatus showing the final position of the collection device tip at the window of the ligand receptor area.

FIG. 6 is an exploded perspective view of the ligand receptor test area.

DESCRIPTION OF THE PREFERRED EMBODIMENTS

In the following description, the apparatus and the method will be described in exemplary terms only, for an antigen determining immunoassay test. This discussion, however, is simply to illustrate the structure and use of the apparatus and the technique and steps of the method. The apparatus clearly can be used for any ligand receptor assay in which washing steps have been eliminated and transfer of reactants to or through a porous membrane or filter is used. The best mode, as described hereinafter, is accordingly, to be considered exemplary and not limiting as to the scope and concept of the invention.

Referring first to FIG. 1 for a general depiction of the apparatus, the inventive apparatus comprises a collection device holder 14 which is comprised of a restrictive portion 1 that hold the shaft of the collection device 2 in place, a cylindrical tube 13 which is comprised of one or more sealed reagent compartments 15 and 20, and a lower ligand receptor reaction area 10.

Referring to FIG. 2, the collection device holder 14 has a nodule 16 which positions onto the cylindrical tube and prevents the apparatus from being accidentally opened. When a sample is to be taken, the collection device holder is removed and separated from the cylindrical tube by twisting and pulling up on the collection device holder. This frees up the collection device holder which is then used to collect the test sample (i.e. throat swab, pus, blood, urethral swab, etc.) by allowing the collection device tip 5 to come in contact with the suspect tissue, fluid, wound, etc.

Referring to FIG. 2 and FIG. 3, after obtaining a test sample, the collection device holder is replaced onto the cylindrical tube 13 and turned until the nodule 4 (FIG. 3) on the cylindrical tube is in alignment with the groove 18. The collection device holder is then manually forced downward until the nodule 4 stops at the horizontal groove 19. When the nodule 4 is in contact with horizontal groove 19, then simultaneously the tip 5 will have broken through the first seal (FIG. 4), mixing with the contents of the first vessel 15, then breaking through seal 7 and emptying its contents into vessel 20. The number of independent compartments is related to the number of required reagent additions and incubation steps. One vessel or a plurality of vessels could be used and the mixing of reagents controlled using the principles of nodules and grooves as previously described. In the preferred embodiment, the collection device holder is turned to the right and then back and forth to mix the contents of vessel 20 through the simultaneous turning of the collection device tip.

Referring to FIG. 2 and FIG. 3, after an appropriate incubation time, the collection device holder 14 is turned to the right and thus aligning nodule 4 (FIG. 3) with groove 3 (FIG. 2) and then manually forced downward until the movement of nodule 4 is stopped by the groove end 21 (FIG. 2). Referring to FIG. 5 and FIG. 6 the lower portion 10 may be physically one piece with the cylindrical tube 13 or an attached separate piece. When the nodule 4 is in contact with the groove end 21, then the collection device tip 5 is in contact with the prefilter membrane 25 through the window 11. The reactants flow through the prefilter membrane through holes 24 of adhesive tape 23 which holds the prefilter membrane 25 against window 11. The shape of the lower portion 10 is configured to enhance contact of the collection device tip with the prefilter or reaction membranes. If preferred, the prefilter could be placed on the inside wall of the window 11. In any case, the reactants flow through holes 21 and 22 of adhesive tape 20 which holds membranes 18 and 19 respectively in place. The holes 21 and 22 restrict the flow of the reactants through a capture membrane 19 and a control membrane 18 and enhances the signal of the reaction by concentrating the labelled ligand or receptor binding pairs into a small area. Absorbant 17 absorbs excess fluid diffusing through the membranes. When an appropriate volume of fluid has diffused through the membranes, usually by saturation of the absorbant, the capture and control membranes are visualized within the holes 21 and 22 respectively by lifting the tab 28 of the adhesive tape 12. Adhesive tape 12 holds the absorbant in place and applies the necessary pressure to ensure diffusion of fluid through the various layers of the ligand receptor test area. The color intensity of the capture membrane 18 is compared to the color intensity of the control membrane 19. A positive result is determined by visualizing a more intense color in the capture membrane than in the control membrane. A negative result is determined by visualizing no significant color or the same weak color in the capture and control membranes. In competitive inhibition assays the positive and negative results are reversed. In the performance of drug analyte assays, the size of the ring of color in a single larger capture membrane is related to the concentration of drug in the test sample. The design of the ligand receptor area, the coating of reagents on the membranes, and the addition or deletion of capture or control membranes are dependent on the particular type of assay being performed. Capture membranes can be coated with antigen or antibody or other complementary ligands or receptors and can be used to determine the presence of different antigens or antibodies. The number of vessels used in the apparatus are dependent upon the type of assay and can contain diluents, media for growth amplification of microorganisms, lyophilized labelled ligands or receptors, etc. The seal 7 (FIG. 4) may be attached to two vessels simultaneously or may be independent. Therefore the vessels could be attached to each other or independent. The following example is illustrative:

EXAMPLE 1

A RAPID IMMUNODIAGNOSTIC TEST FOR GROUP A STREPTOCOCCI

Group C phage associated lysin enzyme which is effective in fragmenting and solubilizing the Group A streptococcal polysaccharide was diluted in a buffer of, 0.05M Citrate phosphate pH 6.1 containing 0.005M EDTA, 0.005M DTT, 0.1% rabbit IgG, 0.05% sodium azide and mixed with Rabbit anti Streptococcal Group A coated gold sol particles (OD518 1.5) diluted in a buffer of 0.02M Tris pH 8.2 containing 1.0% BSA, 0.2% sodium heparin, 0.5% n acetylglucosamine and 0.02% sodium azide in a ratio of 3 parts lysin reagent to 1 part antibody gold sol reagent. The combined reagent was sterile filtered through a 0.2 micron cellulose acetate filter and 200 microliters were aliquoted into acrylic walled reaction cup vessels, having an aluminum foil sealed bottom. The aliquots were frozen and lyophilized. The reaction cup vessels were sealed with aluminum foil and contact cement under nitrogen. Another reaction vessel was cemented to the aluminum foil lid of the first vessel. Two hundred microliters of distilled water was added to the second vessel and then cemented and sealed with aluminum foil. The vessels were placed and positioned into the cylindrical tube. The ligand receptor area was prepared by coating nitrocellulose membranes with rabbit anti group A streptococcal antibody for the capture membranes, and normal rabbit immunoglobulin for the control membranes. The membranes were dried and fixed to a diacetate laminate which had 1.5 mm diameter holes for each membrane. A 1.2 micron cellulose acetate prefilter was used to cover the window of the lower portion of the device. A dacron tipped swab was seeded with varying concentrations of group A streptococci. The swab was placed into the cylindrical tube and forced downward to break the first two seals on the reaction vessels. The swab incubated for 4 minutes at room temperature allowing the lysin enzyme to solubilize the Group A streptococcal polysaccharide and the reaction of the gold labelled anti Group A antibody to form complexes with the released polysaccharide. After four minutes the swab was forced downward through the third seal into the lower portion, coming in contact with the ligand receptor area. The fluid diffused through the prefilter into capture and control membranes. After 30 seconds the tab of the ligand receptor area was pulled away from the lower portion and visuallized. A distinct color reaction with $2 \times 10^3$ organisms of Group A streptococci could be distinguished in the capture membrane compared to the colorless control membrane.

The foregoing disclosure and the showing made in the drawings are merely illustrative of the principles of this invention and are not to be interpreted in a limiting sense. It is understood that through the example and embodiments described herein, that various modifications in light thereof will be suggested to persons skilled in the art to be included in the spirit and review of this application and the scope of the approved claims.

What is claimed is:

1. A self-contained ligand receptor assay device, the combination comprising;
    (a) collection means having an elongated shaft with an absorbent tip for collecting a specimen;
    (b) a tube, cooperative with said collection means, said tube having an interior, an open end and a distal end;
    (c) at least one sealed chamber in said tube;
    (d) a number of reagents equal to the number of said at least one chamber located one reagent in each of said at least one chamber;
    (e) means to seal each said reagent in a respective one of said at least one chamber;
    (f) said seal means comprising frangible seals;
    (g) ligand receptor reaction means including at least one porous membrane;
    (h) means forming a hole in said tube in predetermined spaced relation to said distal end thereof;
    (i) means fixing said ligand receptor reaction means to said tube covering said hole with said least one porous membrane exposed to said interior of said tube; and (j) the length of said shaft being such as to permit said absorbent tip to reach through all of said at least one chamber to mix all of said at least one reagent and to permit fluid diffusion between said tip and said at least one membrane; whereby (k) a labelled ligand or a labelled receptor is immobilized on said ligand receptor reaction means and the result of said assay can be examined.

2. The device of claim 1, further comprises a guiding mechanism for said collection means, said guiding mechanism comprising guide and stop means, nodule means on said tube, and said guide and stop means and said nodule means cooperating with each other causing sequential breaking of said at least one frangible seal and moving said absorbent tip completely through and out of said at least one chamber when said absorbent tip passes through all of said at least one chamber.

3. The device of claim 1, wherein said absorbent tip for collecting a specimen is sterile.

4. The device of claim 1, wherein said at least one porous membrane comprises a plurality of porous membranes at least one membrane of which is coated with different ligands or receptors.

5. The device of claim 1, wherein said at least one reagent comprises a labelled ligand or a labelled receptor.

6. The device of claim 5, wherein said labelled ligand or labelled receptor reagent is lyophilized.

7. The device of claim 5, further comprising at least one other chamber, and microbiological growth media in said other chamber.

8. The device of claim 5, further comprising at least one other chamber, and an extraction reagent for exposing antigenic determinants or hidden epitopes of an antigen, in said other chamber.

9. The device of claim 5, further comprising at least one other chamber, adsorption particles in said other chamber, said absorption particles comprising binders to remove inhibiting or cross reative substances from said assay; and at least one other porous membrane, and (a) said adsorption particles being larger than said labelled ligands or labelled receptors, and (b) said at least one other porous membrane having an effective pore size smaller than said adsorption particles and larger than said labelled ligands or labelled receptors.

10. The device of claim 5, wherein one said at least one chamber contains ligand or receptor coated particles which are larger in mean particle size diameter than said labelled ligand or labelled receptor and the effective pore size of said at least one porous membrane.

11. The device of claim 5 wherein said labelled ligand or labelled receptor reagent comprised a chromophore.

12. The device of claim 11 wherein said chromophore is selected from the group consisting of dyes, dyed particles, pigments, metal sol particles, or dye encapsulated liposomes.

13. The device of claim 12, wherein said chromophore is a metal sol particle selected from the group consisting of gold, silver, or the combination of gold and silver.

* * * * *